United States Patent [19]

Zeeck et al.

[11] Patent Number: 4,861,796

[45] Date of Patent: Aug. 29, 1989

[54] GENTISIC ACID DERIVATIVES HAVING ANTIBIOTIC ACTIVITY

[75] Inventors: Axel Zeeck, Göttingen; Sabine Breiding-Mack, Gross Döhren; Susanne Grabley, Königstein/Taunus; Hartmut Voelskow, Hattersheim am Main; Gerhard Seibert, Darmstadt, all of Fed. Rep. of Germany

[73] Assignee: Hoechst Aktiengesellschaft, Frankfurt am Main, Fed. Rep. of Germany

[21] Appl. No.: 286,046

[22] Filed: Dec. 19, 1988

Related U.S. Application Data

[63] Continuation of Ser. No. 93,184, Sep. 4, 1987, abandoned.

[30] Foreign Application Priority Data

Sep. 8, 1986 [DE] Fed. Rep. of Germany ....... 3630521

[51] Int. Cl.[4] .......................................... A61K 31/195
[52] U.S. Cl. .................................... 514/535; 514/563; 562/453; 560/46; 435/129
[58] Field of Search .................. 562/453; 560/46; 514/535, 563

[56] References Cited

U.S. PATENT DOCUMENTS

| 2,572,284 | 10/1951 | Schoen | 562/453 |
| 3,134,805 | 5/1964 | Tullar | 562/453 |
| 3,238,203 | 3/1966 | Krepcho | 560/46 |
| 4,119,609 | 10/1978 | Allen et al. | 562/453 |

FOREIGN PATENT DOCUMENTS

| 47-32974 | 8/1972 | Japan | 562/453 |
| 694238 | 7/1953 | United Kingdom | 562/453 |
| 694300 | 7/1953 | United Kingdom | 562/453 |
| 704755 | 3/1954 | United Kingdom | 562/453 |

Primary Examiner—James H. Reamer
Attorney, Agent, or Firm—Finnegan, Henderson, Farabow, Garrett & Dunner

[57] ABSTRACT

2-Acetylaminogentisic acid has been isolated from the culture broth after cultivation of a bacterium of the genus Streptomyces. This compound has antibacterial actions against Gram-positive and Gram-negative bacteria.

16 Claims, No Drawings

GENTISIC ACID DERIVATIVES HAVING ANTIBIOTIC ACTIVITY

This is a continuation, of application Ser. No. 093,184, filed Sept. 4, 1987, now abandoned.

A microorganism strain has been isolated from a soil sample, identified as Streptomyces species and deposited at the Deutsche Sammlung von Mikroorganismen (DSM) (German Microorganism Collection), 3400 Göttingen, Grisebachstr. 8, under the number DSM 3814. The strain has the following characteristics:

| | |
|---|---|
| Spore surface: | Sp |
| Spore morphology: | RF/RAa |
| Chromogenicity | M- |
| Color of aerial mycelia: | yellow-gray |

In a nutrient solution containing a source of carbon and nitrogen, together with the customary inorganic salts, the strain DSM 3814 produces 2-acetylaminogentisic acid which has antibiotic activity. Thus, the latter can be obtained by fermentation of the strain DSM 3814, and isolation from the fermentation medium.

2-Acetylaminogentisic acid has antibacterial actions, both against Gram-positive and against Gram-negative bacteria, and can thus be used in appropriate medicines for the treatment of infections caused by bacteria in humans and animals.

Thus the invention relates to:

(1) 2-Acetylaminogentisic acid of the formula I

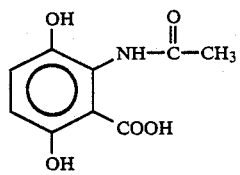

and its derivatives in which, independent of one another, the acetyl group on the 2-amino group can be replaced by $C_1$ or $C_3$-$C_{10}$-acyl, and the carboxyl group in the 3position on the aromatic ring can carry a $C_1$-$C_{10}$-alkyl group The gentisic acid derivatives described above may also be represented by compounds according to the formula Ia

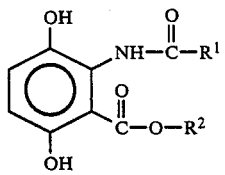

wherein $R^1$ is selected from the group consisting of a hydrogen group or a $C_1$-$C_9$-alkyl group, and $R^2$ is selected from the group consisting of a hydrogen group or a $C_1$-$C_{10}$-alkyl group.

(2) A process for the preparation of the compound of the formula I, which comprises fermentation of Streptomyces species DSM 3814 until the compound of the formula I accumulates in the medium.

(3) The use of the compound of the formula I and its derivatives as active component in medicines.

The invention is illustrated in detail hereinafter and is defined in the patent claims.

Of course, it is also possible to use, in place of the strain DSM 3814, its mutants and variants as long as they produce 2-acetylaminogentisic acid. Mutants of this type can be generated in a manner known per se by physical means, for example irradiation, such as with ultraviolet or X-rays, or chemical mutagens such as, for example, the ethyl ester of methanesulfonic acid (ethyl methanesulfonate, EMS) or 2-hydroxy-4-methoxybenzophenone (MOB).

Sources of carbon which are suitable and preferred for the aerobic fermentation are assimilable carbohydrates and sugar alcohols, such as glucose, lactose or D-mannitol, as well as carbohydrate-containing natural products, such as malt extract. Suitable nutrients containing nitrogen are: amino acids, peptides and proteins and their degradation products, such as peptones or tryptones, as well as meat extracts, ground seeds, for example of corn, wheat, beans, soybeans or the cotton plant, distiller's residues from the production of alcohol, meat meals or yeast extracts, as well as ammonium salts and nitrates. Examples of other inorganic salts which the nutrient solution may contain are chlorides, carbonates, sulfates or phosphates of the alkali metal or alkaline earth metals, iron, zinc and manganese.

2-Acetylaminogentisic acid is produced particularly satisfactorily in a nutrient solution which contains about 2% soybean meal and 2% mannitol, in each case based on the total weight of the nutrient solution. The fermentation is carried out aerobically, that is to say, for example, submerged, with shaking or stirring, in shaken flasks or fermenters, where appropriate with the introduction of air or oxygen. The fermentation can be carried out in a temperature range from about 18° to 35° C., preferably at about 25° to 30° C., in particular at 28° to 30° C. The pH range should be between 6 and 8, advantageously between 6.5 and 7.5. Under these conditions, the culture broth has, in general, a detectable antibiotic action after 1 to 4 days.

The cultivation is advantageously carried out in several stages, i.e. initially one or more precultures are prepared in a liquid nutrient medium and are then transferred into the actual production medium, the main culture, for example in the volume ratio 1:10. The preculture is obtained by, for example, transferring a sporulated mycelium into a nutrient solution and allowing it to grow for about 48 to 72 hours. The sporulated mycelium can be obtained by allowing the strain to grow for about 7 days on a solid or liquid nutrient medium, for example yeast-malt agar.

The progress of the fermentation can be monitored by the pH of the culture, the volume of the mycelium, or by thin-layer chromatography or testing the biological activity.

The 2-acetylaminogentisic acid is isolated from the culture medium by known methods making use of the chemical, physical and biological properties of the products. It is possible to use thin-layer chromatography, for example on silica gel using n-butanol/acetic acid/water as mobile phase, for testing the concentration of antibiotics in the culture medium or in the individual stages of isolation, it being appropriate to compare the amount of antibiotic which has formed with a calibration solution.

The antibiotic can be separated from the filtered culture broth by adsorption onto known adsorber resins, for example polystyrene resins (®)Amberlite XAD 2), preferably at pH 3 to 7, and be obtained by elution with a polar solvent, for example methanol or acetone.

Isolation of the pure product is preferably carried out on suitable media such as hydroxyalkoxypropyldextrans (® Sephadex LH brands), by elution with a lower alkanol, for example methanol, or with a mixture of a lower alkanol and a less polar organic solvent, for example methanol/ethyl acetate, and collection of the fractions having antibiotic activity.

The substance is stable in the solid state and in solution in the pH range 3 to 9, in particular 5 to 8. Thus the compound can be incorporated into customary pharmaceutical formulations.

The compound can be chemically derivatized by methods known per se, for example in such a way that, independently of one another, the acetyl group on the 2-amino group can be replaced by $C_1$ or $C_3$-$C_{10}$-acyl, and the carboxyl group can carry a $C_1$-$C_{10}$-alkyl group, it being possible for each of the hydrocarbon radicals to be saturated or unsaturated, straight-chain or branched, or cyclic aliphatic, aliphatic-aromatic or aromatic and unsubstituted or substituted by halogens, for example chlorine or bromine, or by esterified or etherified hydroxyl groups.

Derivatives of these types also have antimicrobial activity.

The antibacterial action is displayed both against Gram-positive and, in particular, against Gram-negative bacteria, as can be shown, for example, in the agar plate diffusion test in vitro (10 ul/test disk, 6 mm diameter). With sample quantities of 1 ug per plate, the diameters of the zones of inhibition may be found to be 16 mm, for example for *E. coli*.

The invention is illustrated in detail in the examples which follow. Unless otherwise specified, percentage data relates to weight. Unless otherwise stated, mixing ratios for liquids relate to volume.

EXAMPLE 1

(a) Preparation of a suspension of spores of the producer strain DSM 3814

Several malt/yeast extract agar slants (4 g of yeast extract, 10 g of malt extract, 4 g of glucose, and 20 g of agar for solidification, dissolved in 1 l of distilled water, pH 8.0 adjusted before sterilization) are inoculated with Streptomyces spec. DMS 3814 and are incubated at 30° C. for about 6–7 days.

The spores are rinsed out of each tube with 3 ml of liquid [0.9% NaCl and 0.1% polyoxyethylene sorbitan monooleate ((®) Tween 80) in distilled water]. The suspensions are combined and stored at 4° C. until the main cultures are inoculated.

(b) Preparation of a preculture of the producer strain DSM 3814 in Erlenmeyer flasks 5 Erlenmeyer flasks (300 ml capacity) each containing 100 ml of nutrient solution (40 g of glucose, 30 g of soybean meal, 2.5 g of NaCl, 2.5 g of $CaCO_3$, dissolved in 1 l of distilled water, pH 7.5 adjusted before sterilization) are each inoculated with 1.5 ml of the spore suspension (for example 1a), fresh if possible, and incubated at 30° C. in a shaker (180 rpm) for 72 hours.

(c) Preparation of a Main Culture of the Producer Strain DSM 3814

A 300 ml Erlenmeyer flask containing 100 ml of nutrient solution (20 g of soybean meal, 20 g of mannitol, dissolved in 1 l of distilled water, pH 7.5 adjusted before sterilization) is inoculated with 3 ml of the preculture and is incubated at 30° C. in a shaker (180 rpm).

The production maximum is reached after about 30 hours.

The yields of 2-acetylaminogentisic acid are about 10 mg/l.

EXAMPLE 2

Fermentation of the Producer Strain in a Fermenter

A fermenter with a capacity of 10 l is operated under the following conditions:

At an incubation temperature of 30° C. and with the stirrer at 600 rpm, about 7 l of air are passed per minute into the culture liquid (medium as in Example 1c). The fermenter is inoculated with 500 ml of the preculture (see Example 1b).

The production optimum is reached after about 30 hours. The culture has a pink-brown coloration.

The yields of 2-acetylaminogentisic acid are about 10 to 50 mg/l.

EXAMPLE 3 Isolaiton of 2-Acetylaminogentisic Acid

The mycelium which has been obtained as in Example 2 is pressed off and discarded, and the culture filtrate is freeze-dried and then extracted twice with 2 l of methanol each time. The methanol extracts are combined and evaporated almost to dryness in vacuo. The residue is suspended in about 100 ml of methanol, and then an equal amount of ethyl acetate is added, insolubles are allowed to settle out, and the supernatant is chromatographed on a silica gel column (30 × 10 cm) with ethyl acetate/methanol (4:1). The fractions containing the antibiotic are combined and, after a further separation on Sephadex LH 20 with methanol/water (9:1; v:v), 85 mg of 2-acetylaminogentisic acid are obtained in pure form. The product is soluble in methanol but not in chloroform.

It can be identified on the basis of the following data:
Thin-layer chromatography:

| Mobile phase: | | $R_F$ values |
| --- | --- | --- |
| Ethyl acetate/methanol/water (6:2:1) | | 0.7 |
| Ethyl acetate/methanol/water (9:1:0.5) | | 0.2 |
| Ethyl acetate/methanol (4:1) | | 0.35 |
| UV: $\lambda_{max}$ /nm/ | = 340, 219 252 sh | in MeOH and MeOH + 2 N HCl |
| | = 340, 223 252 sh | in MeOH + 2 N NaOH |

IR (KBr disk): 3470, 3050–2800, 1687, 1635 sh, 1600, /cm$^{-1}$/ 1562, 1478, 1356, 1306, 1271, 1233.

$^1$H NMR (200 MHz in d$_6$-DMSO): δ2.19 (s, 3H); 6.49 (d, 9Hz, 1H); 6.76 (d, 9HZ, 1H); 9.76 (s, OH); 14.58 (s, broad, NH); 15.12 (s, OH) ppm.

$^{13}$C NMR (50 MHz in CD$_3$OD); δ24.0 (CH$_3$); 109.5 (q, C); 115.2 (CH); 124.3 (CH); 128.9 (q, C); 141.4 (q, C); 157.2 (q, C); 172.7 (CO); 176.3 (COOH) ppm.

What is claimed:

1. Acetylaminogentisic acid of the Formula I.

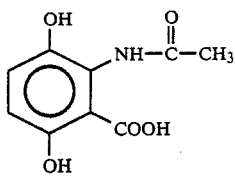

I

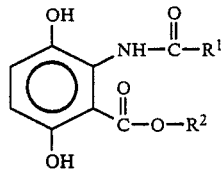

Ia wherein $R^1$ is selected from the group consisting of a hydrogen group or a $C_1-C_9$-alkyl group, and $R^2$ is selected from the group consisting of a hydrogen group or a $C_1-C_{10}$-alkyl group.

2. A method of treating a mammal for a gram-positive bacterial infection, which comprises administering to said mammal a compound according to claim 1 in an amount effective to treat said bacterial infection.

3. A method according to claim 2, wherein the mammal is a human being.

4. A method according to claim 2, wherein the mammal is a non-human mammal.

5. A method of treating a mammal for a gram-negative bacterial infection, which comprises administering to said mammal a compound according to claim 1 in an amount effective to treat said bacterial infection.

6. A method according to claim 6, wherein the mammal is a human being.

7. A method according to claim 6, wherein the mammal is a non-human mammal.

8. A pharmaceutical composition useful in treating or preventing a bacterial infection in a mammal, which comprises an effective amount of compound according to claim 1 and one or more pharmaceutically acceptable carriers.

9. A compound according to Formula Ia

10. A method of treating a mammal for a gram-positive bacterial infection, which comprises administering to said mammal a compound according to claim 9 in an amount effective to treat said bacterial infection.

11. A method according to claim 10, wherein the mammal is a human being.

12. A method according to claim 11, wherein the mammal is a non-human mammal.

13. A method of treating a mammal for a gram-negative bacterial infection, which comprises administering to said mammal a compound according to claim 9 in an amount effective to treat said bacterial infection.

14. A method according to claim 13, wherein the mammal is a human being.

15. A method according to claim 13, wherein the mammal is a non-human mammal.

16. A pharmaceutical composition useful in treating or preventing a bacterial infection in a mammal, which comprises an effective amount of compound according to claim 9 and one or more pharmaceutically acceptable carriers.

* * * * *

UNITED STATES PATENT AND TRADEMARK OFFICE
CERTIFICATE OF CORRECTION

PATENT NO. : 4,861,796

DATED : August 29, 1989

INVENTOR(S) : Axel Zeeck et al.

It is certified that error appears in the above-identified patent and that said Letters Patent is hereby corrected as shown below:

Claim 1, column 4, line 68, change "Acetylaminogentisic" to --2-Acetylaminogentisic--.

Signed and Sealed this

Fifteenth Day of October, 1991

Attest:

HARRY F. MANBECK, JR.

*Attesting Officer*  *Commissioner of Patents and Trademarks*